United States Patent [19]
Kudoh et al.

[11] Patent Number: 5,466,703
[45] Date of Patent: Nov. 14, 1995

[54] INSECTICIDAL AND MITICIDAL COMPOSITION

[75] Inventors: Kichizo Kudoh; Yasuo Kikuchi; Tatsuya Ishida; Tatsufumi Ikeda, all of Nagano; Hiroaki Fujimoto, Toyonaka, all of Japan

[73] Assignee: Sumitomo Chemical Company, Limited, Osaka, Japan

[21] Appl. No.: 310,326

[22] Filed: Sep. 22, 1994

[30] Foreign Application Priority Data

Sep. 22, 1993 [JP] Japan .................................. 5-257495

[51] Int. Cl.$^6$ .......................... A01N 37/34; A01N 43/76; A01N 53/00
[52] U.S. Cl. .......................... 514/374; 514/521; 514/531
[58] Field of Search ................................ 514/374, 521, 514/531

[56] References Cited

U.S. PATENT DOCUMENTS 3,835,176  9/1974  Matsuo et al. ...................... 260/465 D

FOREIGN PATENT DOCUMENTS

| 56-152451 | 11/1981 | Japan . |
| 59-181241 | 10/1984 | Japan . |
| 62-212335 | 9/1987 | Japan . |
| 9200559 | 1/1992 | WIPO . |
| WO9322297 | 11/1993 | WIPO . |

OTHER PUBLICATIONS

Suzuki et al., C.A., vol. 920 (Mar. 28, 1994) 120: 164,157d.
Worthing et al., "The Pesticide Manual", 9th ed. (1990) p. 377.
1992 *Farm Chemicals Handbook*, Pesticide Dictionary . . . , pp. A 6, C 294–C 295.

*Primary Examiner*—Allen J. Robinson
*Attorney, Agent, or Firm*—Birch, Stewart, Kolasch & Birch

[57] ABSTRACT

The invention provides an insecticidal and miticidal composition containing 2-(2,6-difluorophenyl)-4-(2-ethoxy-4-tertiarybutylphenyl)-2-oxazoline and at least one compound selected from the specific pyrethroid compounds, as its active ingredients.

The present composition can protect useful plants from various kinds of noxious insects and mites such as Aphididae and Acarina in small application amounts.

11 Claims, No Drawings

INSECTICIDAL AND MITICIDAL COMPOSITION

FIELD OF THE INVENTION

The present invention relates to an insecticidal and miticidal composition containing, as its active ingredients, 2-(2,6-difluorophenyl)-4-(2-ethoxy- 4-tertiarybutylphenyl)-2-oxazoline (referred to as Compound A, hereinafter) and specific pyrethroid compounds.

DESCRIPTION OF THE RELATED ART

Insecticides and miticides for controlling various kinds of noxious insects such as agricultural, gardening, forest, livestock and hygiene insects have been developed and various insecticides and/or miticides have been in use.

However, the conventional insecticides and miticides have not been always satisfactory in their lethal activity, rapid action and/or residual activity. In addition, greater amounts of the insecticides and/or miticides are required for effective control, because some of the insects and mites acquire resistance to conventional agents.

Therefore, there have been demands for an insecticide and/or miticide having good lethal activity, rapid action and good residual activity against noxious insects and mites including resistant ones at lower concentrations.

Under the circumstances, the present inventors have examined various combinations of 2-(2,6-difluorophenyl)-4-(2-ethoxy-4-tertiarybutylphenyl)-2-oxazoline (Compound A) and existing insecticidal and miticidal compounds, and found that a composition containing Compound A and specific pyrethroid compounds exhibits unexpected synergistic insecticidal and miticidal activity against noxious insects and mites including resistant ones as compared with single usage of each of the compounds and with combinations of Compound A and other pyrethroid compounds.

SUMMARY OF THE INVENTION

Thus the present invention provides an insecticidal and miticidal composition comprising as its effective ingredients, Compound A and at least one pyrethroid compound selected from the group consisting of (1) 2-methyl-2-(4-bromodifluoromethoxyphenyl)propyl 3-phenoxybenzyl ether (referred to as Compound 1, hereinafter), (2) cyano(3-phenoxyphenyl)methyl 2,2-dimethyl-3-[ 3-oxo-3-{2,2,2-trifluoro-1-(trifluoromethyl)ethoxy}-1 -propenyl]cyclopropanecarboxylate (referred to as Compound 2, hereinafter), (3) α-cyano-3-phenoxybenzyl 2,2,3,3-tetramethylcyclopropanecarboxylate (referred to as Compound 3, hereinafter), (4) α-cyano-3-phenoxybenzyl-N-(2-chloro-α,α,α-trifluoro-p-tryl)valinate (referred to as Compound 4, hereinafter), and (5) 2-methylbiphenyl-3-ylmethyl 3-(2-chloro-3,3,3-trifluoro-prop- 1-enyl)-2,2-dimethylcyclopropanecarboxylate (referred to as Compound 5, hereinafter).

PREFERRED EMBODIMENT OF THE INVENTION

The present composition exhibits excellent lethal activity, rapid action and residual activity against noxious insects and mites such as Acarina and Aphididae in a considerably small amount while the active ingredients of such composition, when used singly, can seldom control them in the same amount. The present composition can also effectively control resistant insects and mites.

Compound A in the present composition is a known compound described in PCT Application Laid-Open No. WO92/00559.

Some of the active ingredients of the present composition may possess stereoisomers or geometrical isomers, hence the present composition may include such isomers and mixtures thereof.

Examples of such isomers are as follows:

[1R-{1α(s*), 3α(Z)}]-cyano(3-phenoxyphenyl)methyl 2,2-dimethyl-3-[3-oxo-3-(2,2,2-trifluoro-1-(trifluoromethyl)ethoxy}- 1-propenyl]cyclopropanecarboxylate (referred to as Compound 2a, hereinafter);

(RS)-α-cyano-3-phenoxybenzyl 2,2,3,3-tetramethylcyclopropanecarboxylate (referred to as Compound 3a, hereinafter);

(RS)-α-cyano-3-phenoxybenzyl N-(2-chloro-α,α,α-trifluoro-p-tolyl)-D-valinate (referred to as Compound 4a, hereinafter); and 2-methylbiphenyl-3-ylmethyl (Z)(1RS)-cis-3-(2-chloro-3,3,3-trifluoroprop-1-enyl)-2,2-dimethylcyclopropanecarboxylate (referred to as Compound 5a, hereinafter).

Compound 1 and Compounds 2a–5a have been known under common names of fubphenblocks, acrinathrine, phenpropathrine, fluvalinate and biphenthrine respectively. Compound 1 is disclosed in Japanese Patent Kokai (Laid-Open) No. S62-212335, and Compound 2a is described in Farm Chemicals Handbook, C 294–C 295 (1992) by Meister Publishing Company. Compounds 3a, 4a and 5a are disclosed in Japanese Patent Kokai (Laid-Open) Nos., S48-10225, S56-152451 and S59-181241 respectively.

The present composition can be widely used as a controlling agent for noxious insects and mites of agricultural, or gardening crops or trees, livestock or hygiene.

Examples of such noxious pests that the present composition can control are as follows.

Acarina: Acari such as *Tetranychus urticae, Tetranychus kanzawai, Tetranychus cinnabarinus, Panonychus citri, Panonychus ulmi, Panonychus mori, Tetranychus viennensis, Eotetranychus carpini, Aculops pelekassi, Calacarus carinatus, Epitrimerus pyri;* Acari belonging to Tetranychidae, Eriophyidae or Tenuipalpidae, which are parasitic on various kinds of fruit trees such as oranges, apples, pears, peaches, grapes, chestnuts and apricots, vegetables such as eggplants, cucumbers and strawberries, beans such as soybeans, adzuki beans and kidney beans, commercial crops like tea and cotton, gardening plants such as roses, carnations, tulips and cyclamens, and trees such as pine trees and Japan cedars;

Ixodidae such as *Haemaphysalis longicornis, Ixodes ovatus* and *Boorphilus microplus;* Acaridae such as *Tyrophagus putrescentiae* and *Dermatophagoides farinae* and house dust mites such as *Pyroglyphidae, Cheyletidae* and *Bdellonyssus bacoti.*

Lepidoptera including: Phyralidae such as *Chilo suppressalis, Cnaphalocrocis medinalis, Plodia interpunctella* and *Ostrinia furnacalis;* Noctuidae such as *Spodoptea litura, Pseudolaletia separata* and *Mamestera brassicae;* Pieridae such as *Pieris rapae crucivora;* Tortricidae such as Adoxophyes spp., *Adoxophyes orana* and Carposinidae; Lyonetiidae such as *Phyllocnistis citrella;* Lithocolletidae, Gelechiidae, Lymantriidae and Gracillariidae such as *Phyllonorycter ringoniella;* Agrotis spp. such as *Agrotis segetum* and *Agrotis ipsilon;* Heliothis spp.; and Tineidae such as *Plutella xylostella* and *Tinea translucens.*

Diptera including Culicidae such as *Culex pipiens* and *Culex tritaeniorhynchus;* Aedes spp. such as *Aedes aegypti* and *Aedes albopictus;* Anopheles spp. such as *Anopheles sinensis;* midges (Chironomidae); Muscidae such as *Musca domestica* and *Muscina stabulans;* Calliphoridae; Sarcophagidae; Anthomyiidae such as *Fannia canicularis, Delia platura* and *Delia antigua;* Cecidomyiidae; Tephritidae such as *Dacus cucurbitae;* Agromyzidae such as *Agromyza oryzae;* and Ephydridae, Drosophilidae, Psychodidae, Tabanidae, Simullidae and *Stomoxyidae calcitrans;*

Hemiptera including: Aphididae such as *Myzus persicae, Aphis gossypii, Aphis citricola, Aphis pomi, Lipaphis pseudobrassicae, Nippolachnus piri, Toxoptera aurantii,* and *Toxoptera ciicidus;* Delphacidae such as *Laodelphax striatellus, Nilaparvata lugens* and *Sogatella furicfera;* Cicadellidae such as *Nephotettix cincticeps, Empoasca onukii* and *Arboridia apicalis;* Aleyrodidae such as *Trialeurodes vapoariorum, Bemisia tabaci* and *Aleurotrixus flococcus;* Psyllidae such as *Psylla piri* and *Psylla mali;* Pentatomidae (stink bugs) such as *Eysarcoris parvus, Eysarcoris ventalis, Nezara antennata, Cletus punctiger, Riptortus clavatus* and *Plautia stali;* Pseudococcidae such as *Saissetia olea, Unaspis yanonensis* and *Pseudococcus comstocki;* and Tingidae.

Dermaptera including; corn root worms such as *Diabrotica virgifera* and *Diabrotica undecimpunctata;* Hydrophilidae such as *Anomala cuprea* and *Anomala rufocurea;* Curculionidae such as *Sitophilus zeamais, Lissorhoptrus oryzophilus, Echinocnemus squameus* and *Callosobruchus chinensis;* Neatus picipes such as *Tenebrio molitor* and *Tribolium castaneum;* Chrysomelidae such as *Leptinotarsa decemlineata, Phyllotreta striolata, Aulacophora femoralis* and *Oulema oryzae;* Anobiidae; Epilachuna spp. such as *Epilachuna vigintioctopunctata, Epilachuna vigintioctomaculata;* and Lyctidae, Bostrychidae and Cerdmbycidae.

Blattodea such as *Periplaneta japonica, Periplaneta americana, Periplaneta fuliginosa, Periplaneta brunnea, Blattela germanica* and *Blatta orientalis.*

Thysanoptera such as *Scirtothrips dorsalis, Thrips palmi, Ponticulothrips diospyrosi, Thrips hawaiiensis* and *Frankliniella occidentalis.*

Hymenoptera including Formicidae and Symphyta such as *Athalia rosae ruficornis.*

Orthoptera including Gryllotalpidae, *Oxya yezoenisi* and *Locusta migratoria.*

Aphaniptera, for example, *Pulex irritans, Ctenocephalides canis* and *Ctenocephalides felis.*

Phthiraptera, for example, *Pediculus humanus capitis* and *Phthirus pubis.*

Isoptera, for example, *Reticulitermes speratus* and *Coptotermes formosanus.*

The present composition exhibits rapid action and residual activity, particularly upon eggs, larvae and adults of Tetranychidae on vegetables, fruit trees and trees and upon Aphididae, which are noxious insects belonging to Hemiptera.

The present composition can be used as it is, i.e., the combination of Compound A and the specific pyrethroid compound (1–5) alone, but the ingredients of the present composition are preferably supported by various inactive carriers in a form of liquid, solid or gas. Moreover, additives such as surfactant, dispersing agent, sticking agent, stabilizer and propellants may be added, if necessary, to prepare formulations such as dusts, granules, emulsions, oil solutions, wettable powders, sols, flowables, aerosols, coating agents, fumigants, smoking agents and ULV (formulations for ultra low volume agents).

Liquid carriers mentioned above include: water; aromatic hydrocarbons such as xylene, toluene, benzene and dimethylnaphthalene; chlorinated hydrocarbons such as chlorobenzene, dichloromethane, chloroethylene and carbontetrachloride; aliphatic or alicyclic hydrocarbons such as benzine, cyclohexane and hexane; alcohols such as ethanol, propanol and butanol; and ketones such as acetone, methylethylketone and cyclohexanone.

Examples of solid carriers are: natural mineral powders such as bentonite, talc, clay, kaolin, montmorillonite, diatomite and calcium carbonate; and synthetic mineral powders such as alumina and silicate.

Surfactants include alkyl sulfates, alkyl sulfonates, polyoxyethyleneglycol ethers, polyoxyethyleneglycol esters and polyhydric alcohol esters.

Sticking agents and dispersing agents include casein, gelatin, gum arabic, alginic acid, lignin, bentonite and polyvinylalcohol.

Examples of stabilizers are PAP (isopropyl acidic phosphate), BHT (2,6-di-tertiary-butyl-4-methylphenol), TCP (tricresyl phosphate), vegetable oils, mineral oils, surfactants, fatty acids or esters thereof.

Propellants include, for example, liquefied petroleum gas, dimethyl ether and fluorocarbon.

The mixing ratio of the active ingredients of the present composition, i.e., Compound A and pyrethroid compounds (1–5), is not limited particularly and may be widely varied depending on kinds, formulation forms and purposes of the application of the composition. But the amount of pyrethroid compounds is preferably within a range of from 0.01 to 30 parts by weight, more preferably 0.1 to 20 parts by weight, per 1 part by weight of Compound A and the total content of both active ingredients contained in the present composition is preferably within a range of from 0.01 to 90% by weight, more preferably from 0.1 to 80% by weight.

Application amount of the present composition may be different depending on formulation forms, time, place and way of application, kinds of noxious organisms and degree of damage. The application amount is usually within a range of from about 0.1 to 1000 g, preferably from 5 to 500 g per 10a in terms of active ingredients contained in the composition.

The application of the present composition may be conducted by way of, for instance, spraying, vaporizing, dusts spraying, granule scattering and fumigation directly or using apparatuses to noxious insects or places where noxious insects propagate. Further the present composition can be incorporated with other insecticides, nematodicides, miticides, disinfectants, herbicides, plant-growth regulators, fertilizers, soil improvers, synergists and feeds for animals, or can be used simultaneously with the above-mentioned agents instead of incorporation.

EMBODIMENTS

The present composition will be explained in detail below with reference to Formulation Examples and Biological Test Examples, but the scope of the present invention may not be limited thereto. Meanwhile "parts" in the Formulation Examples means "parts by weight".

Formulation Example 1

Dusts 3 parts of Compound A, 2 parts of Compound 1, 45 parts of talc and 50 parts of clay are mixed homogeneously and pulverized to yield dust. In the same way, dusts were prepared using Compound 2a, 3a, 4a or 5a in place of Compound 1 respectively. Thus prepared dusts can be sprayed directly to plants in amounts of 1–5 kg per 10a by means of a dust spraying apparatus respectively.

Formulation Example 2

Emulsions 5 parts of Compound A, 5 parts of Compound 3a, 8 parts of polyoxyethylenealkyl aryl ether, 2 parts of sodium alkyl arylsulfonate and 80 parts of xylene are mixed homogeneously to yield an emulsion. In the same way emulsions are prepared using Compound 1, 2a, 4a, or 5a in place of Compound 3a respectively. Thus prepared emulsions can be respectively sprayed, after being diluted 1000–5000 times, in amounts of 100–600 l per 10a.

Formulation Example 3

Wettable Powders 5 parts of Compound A, 10 parts of Compound 2a, 3 parts of sodium alkylbenzenesulfonate, 3 parts of sodium ligninsulfate and 79 parts of diatomite are mixed and pulverized homogenously by means of jet-airmill to yield wettable powders. In the same way, wettable powders are prepared using Compound 1, 3a, 4a, or 5a instead of Compound 2a respectively. Thus prepared wettable powders can be sprayed, after being diluted 500–3000 times, in amounts of 100–600 l per 10a respectively.

Formulation Example 4

Flowables 5 parts of Polyoxyethylenestyrylphenylethersulfate, 20 parts of 1% aqueous solution of Xantan gum, 3 parts of mineral matter of smectite type and 62 parts of water are dissolved uniformly, to which 5 parts of Compound A and 5 parts of Compound 3a are added and stirred well. The resultant mixture is wet-grounded by means of sand mill to yield a flowable agent. In the same way flowables are prepared using Compound 1, 2a, 4a or 5a instead of Compound 3a respectively. Thus obtained flowables can be respectively sprayed, after being diluted 1000–5000 times, in amounts of 100–600 l per 10a in actual application.

Formulation Example 5

Heat-Smoking Agents 50 mg of a pyrethroid compound, Compound 1, 2a, 3a, 4a or 5a, and 50 mg of Compound A are dissolved in appropriate amounts of acetone. Ceramic plates of 4.0 cm×4.0 cm and 1.2 cm thick are immersed in the resultant solutions respectively to yield heat-smoking agents.

Biological Test Example 1

Ovicidal Test for *Tetranychus urticae*

6 ml of the test solution containing given amounts of active ingredients prepared according to the above-described Formulation Example 2 (Emulsions), were sprayed to leaves of *Phaseolus vulgaris* on which eggs (3–4-day instar) of *Tetranychus urticae* were laid. 4 Days after the drug application, hatching of the eggs was examined to determine the ovicidal ratio. Meanwhile the theoretical ovicidal ratio (%) and the synergistic effect index (%) were determined from the following equation.

$$\text{Theoretical ovicidal ratio (\%)} = A + \{(100 - A) \times B\}/100 \quad \text{Equation 1}$$

Synergistic effect index (%) =

{Ovicidal ratio (%)/Theoretical ovicidal ratio (%)} × 100 wherein A stands for ovicidal ratio (%) of Compound A and B stands for respective ovicidal ratios (%) of Compound 1 and Compounds 2a, 3a, 4a, and 5a.

The results are shown in Table 1.

TABLE 1

| Test Compound | Amounts of active components (ppb) | Ovicidal ratio (%) | Theoretical ovicidal ratio (%) | Synergistic effect index (%) |
|---|---|---|---|---|
| Compound A + 1 | 25 + 25 | 46.8 | 24.3 | 192 |
|  | 25 + 50 | 96.5 | 25.2 | 382 |
|  | 25 + 100 | 100.0 | 28.7 | 348 |
| Compound A + 2a | 25 + 25 | 52.0 | 25.5 | 204 |
|  | 25 + 50 | 91.3 | 24.5 | 373 |
|  | 25 + 100 | 100.0 | 27.1 | 370 |
| Compound A + 3a | 25 + 25 | 43.3 | 27.4 | 158 |
|  | 25 + 50 | 79.4 | 25.9 | 307 |
|  | 25 + 100 | 100.0 | 29.5 | 339 |
| Compound A + 4a | 25 + 25 | 63.7 | 24.1 | 264 |
|  | 25 + 50 | 95.2 | 25.6 | 372 |
|  | 25 + 100 | 96.7 | 31.0 | 312 |
| Compound A + 5a | 25 + 25 | 45.7 | 25.6 | 179 |
|  | 25 + 50 | 93.3 | 24.1 | 387 |
|  | 25 + 100 | 97.5 | 27.4 | 356 |
| Compound A | 25 | 24.1 | — | — |
| Compound 1 | 25 | 0.3 | — | — |
|  | 50 | 1.5 | — | — |
|  | 100 | 6.1 | — | — |
| Compound 2a | 25 | 1.8 | — | — |
|  | 50 | 0.5 | — | — |
|  | 100 | 3.9 | — | — |
| Compound 3a | 25 | 4.4 | — | — |
|  | 50 | 2.4 | — | — |
|  | 100 | 7.1 | — | — |
| Compound 4a | 25 | 0.0 | — | — |
|  | 50 | 2.0 | — | — |
|  | 100 | 9.1 | — | — |
| Compound 5a | 25 | 2.0 | — | — |
|  | 50 | 0.0 | — | — |
|  | 100 | 4.4 | — | — |
| Non-treated zone | — | 2.0 | — | — |

Biological Test Example 2

Ovicidal Test for Resistant *Tetranychus kanzawai*

6 ml of the test solutions containing given amounts of active ingredients, prepared according to the Formulation Example 4 (Flowables) above, were sprayed to leaves of *Phaseolus vulgaris* on which eggs (3–4-day instar) of resistant *Tetranychus kanzawai* were laid. 4 Days after the drug application, hatching of the eggs was examined to determine the ovicidal ratio. Meanwhile, the theoretical ovicidal ratio (%) and the synergistic effect index (%) were determined from the following equation.

$$\text{Theoretical ovicidal ratio (\%)} = A + \{(100 - A) \times B\}/100 \quad \text{Equation 2}$$

Synergistic effect index (%) =

-continued $$\{\text{Ovicidal ratio (\%)/Theoretical ovicidal ratio (\%)}\} \times 100$$

wherein A stands for ovicidal ratio (%) of Compound A and B stands for ovicidal ratios (%) of Compound 1 and Compounds 2a, 3a, 4a and 5a respectively.

The results obtained are shown in Table 2.

TABLE 2

| Test Compound | Amounts of active components (ppb) | Ovicidal ratio (%) | Theoretical ovicidal ratio (%) | Synergistic effect index (%) |
|---|---|---|---|---|
| Compound A + 1 | 250 + 250 | 49.9 | 21.7 | 229 |
|  | 250 + 500 | 92.3 | 20.8 | 443 |
|  | 250 + 1000 | 98.5 | 22.4 | 440 |
| Compound A + 2a | 250 + 250 | 60.3 | 23.1 | 261 |
|  | 250 + 500 | 85.0 | 19.6 | 433 |
|  | 250 + 1000 | 100.0 | 22.2 | 451 |
| Compound A + 3a | 250 + 250 | 66.7 | 21.6 | 309 |
|  | 250 + 500 | 89.2 | 22.6 | 394 |
|  | 250 + 1000 | 97.6 | 21.3 | 459 |
| Compound A + 4a | 250 + 250 | 71.5 | 20.1 | 355 |
|  | 250 + 500 | 98.3 | 20.7 | 475 |
|  | 250 + 1000 | 95.4 | 19.8 | 482 |
| Compound A + 5a | 250 + 250 | 51.1 | 20.9 | 244 |
|  | 250 + 500 | 72.9 | 20.0 | 364 |
|  | 250 + 1000 | 88.4 | 21.1 | 419 |
| Compound A | 250 | 18.4 | — | — |
| Compound 1 | 250 | 4.1 | — | — |
|  | 500 | 3.0 | — | — |
|  | 1000 | 4.9 | — | — |
| Compound 2a | 250 | 5.8 | — | — |
|  | 500 | 1.5 | — | — |
|  | 1000 | 4.6 | — | — |
| Compound 3a | 250 | 3.9 | — | — |
|  | 500 | 5.2 | — | — |
|  | 1000 | 3.5 | — | — |
| Compound 4a | 250 | 2.1 | — | — |
|  | 500 | 2.8 | — | — |
|  | 1000 | 1.7 | — | — |
| Compound 5a | 250 | 3.1 | — | — |
|  | 500 | 2.0 | — | — |
|  | 1000 | 3.3 | — | — |
| Non-treated zone | — | 3.2 | — | — |

Biological Test Example 3

Pot-Plant Test for *Tetranychus urticae*

*Tetranychus urticae* was propagated on kidney bean planted in a pot (20 cm diameter). Just before spraying the drug, numbers of female adults which were parasitic thereon were counted. Test solutions of a given concentrations prepared according to the Formulation Example 2 (Emulsion) were sprayed to the stems and leaves of the kidney beans. After air-drying the pots were kept at room temperature and the numbers of female adults of *Tetranychus urticae* parasitic thereon were counted on certain predetermined days. Corrected density indices were respectively calculated from the following equation, and results are shown in Table 3.

$$\text{Corrected density index} = \frac{\substack{\text{Number of mites} \\ \text{before spraying} \\ \text{in case of no} \\ \text{application}} \times \substack{\text{Number of mites} \\ \text{after spraying in} \\ \text{case of drug} \\ \text{application}}}{\substack{\text{Number of mites} \\ \text{after spraying} \\ \text{in case of no} \\ \text{application}} \times \substack{\text{Number of mites} \\ \text{before spraying in} \\ \text{case of drug} \\ \text{application}}} \times 100 \quad \text{Equation 3}$$

TABLE 3

| Test Compound | Concentration (ppm) | Corrected density index | | | |
|---|---|---|---|---|---|
|  |  | 3-day | 10-day | 20-day | 30-day |
| Compound 1 | 25 | 14.0 | 3.9 | 3.9 | 3.9 |
| Compound 2a | 25 | 12.8 | 2.6 | 5.8 | 6.6 |
| Compound 3a | 25 | 14.8 | 8.0 | 3.0 | 7.9 |
| Compound 4a | 25 | 19.9 | 7.2 | 3.0 | 4.2 |
| Compound 5a | 25 | 6.9 | 2.7 | 1.3 | 2.6 |
| Compound A | 25 | 40.3 | 10.4 | 2.9 | 5.3 |
| Compound A + 1 | 25 + 25 | 3.4 | 0 | 0 | 0 |
| Compound A + 2a | 25 + 25 | 7.9 | 0 | 0 | 0.7 |
| Compound A + 3a | 25 + 25 | 2.3 | 0.5 | 0 | 0 |
| Compound A + 4a | 25 + 25 | 3.4 | 1.2 | 0 | 0 |
| Compound A + 5a | 25 + 25 | 4.7 | 0.7 | 0 | 0 |
| Non-treated zone | — | 100 | 100 | 100 | 100 |

Biological Test Example 4

Pot-Plant Test for Resistant *Tetranychus kanzawai*

*Tetranychus kanzawai* having resistance against various insecticides and/or miticides was propagated on tea trees planted in pots (20 cmφ). Just before spraying, numbers of female adults which were parasitic thereon were counted respectively. Test solutions of given concentrations prepared according to the aforementioned Formulation Example 4 (Flowable agent) were sprayed to the tea trees. After air-drying, the pots were kept at room temperature and the numbers of female adults of *Tetranychus kanzawai* were counted on predetermined days respectively. Corrected density indices were determined from the above-described equation respectively, of which results are shown in Table 4.

TABLE 4

| Test Compound | Concentration (ppm) | Corrected density index | | | |
|---|---|---|---|---|---|
|  |  | 3-day | 10-day | 20-day | 30-day |
| Compound 1 | 25 | 11.6 | 5.7 | 4.9 | 4.1 |
| Compound 2a | 25 | 8.0 | 5.1 | 6.0 | 5.7 |
| Compound 3a | 25 | 19.2 | 7.1 | 6.4 | 5.2 |
| Compound 4a | 25 | 14.6 | 8.6 | 2.7 | 4.1 |
| Compound 5a | 25 | 14.9 | 5.6 | 2.9 | 3.6 |
| Compound A | 25 | 45.7 | 10.5 | 2.9 | 3.3 |
| Compound A + 1 | 25 + 25 | 3.4 | 0 | 0 | 0 |
| Compound A + 2a | 25 + 25 | 6.3 | 1.0 | 0 | 0.2 |
| Compound A + 3a | 25 + 25 | 2.8 | 0.9 | 0 | 0 |
| Compound A + 4a | 25 + 25 | 5.8 | 1.8 | 0 | 0.1 |
| Compound A + 5a | 25 + 25 | 5.6 | 2.6 | 0 | 0 |
| Non-treated zone | — | 100 | 100 | 100 | 100 |

Biological Test Example 5

Pot-Plant Test for *Tetranychus urticae*

*Tetranychus urticae* was propagated on *Phaseolus vulgaris* planted in pots (20 cmφ). Just before spraying, numbers of female adults of *Tetranychus urticae* which were parasitic thereon were counted respectively. Test solutions of given concentrations prepared according to the aforementioned Formulation Example 2 (Emulsion) were sprayed to stems and leaves of *Phaseolus vulgaris*. After air-drying, the pots were kept at room temperature. 4 Days after the drug spraying, the numbers of female adults of *Tetranychus urticae* parasitic thereon were counted to determine the survival rate.

The survival rate was determined from the following equation.

$$\text{Survival rate } (\%) = (C_0 \times T_4 / T_0 \times C_4) \times 100 \quad \text{Equation 4}$$

wherein $C_0$ and $C_4$ respectively denote numbers of female adults in the non-treated zone before drug treatment and after 4 days, and $T_0$ and $T_4$ respectively denote numbers of female adults in the treated zone before treatment and 4 days after the treatment.

The results obtained are shown in Table 5.

Meanwhile compounds used in the test as controls are expressed by the following compound symbols:

Compound X: (RS)-α-cyano-3-phenoxybenzyl (RS)-2-(4-chlorophenyl)-3-methylbutyrate (common name: fenvalerate) Compound Y: 3-phenoxyphenylmethyl (±)cis, trans-3-(2,2-dichloroethenyl)-2,2-dimethylcyclopropanecarboxylate (common name: permethrin)

TABLE 5

| Test Compound | Amount of active component (ppm) | Survival rate (%) |
| --- | --- | --- |
| Compound A + X | 100 + 100 | 24.4 |
| Compound A + Y | 100 + 100 | 58.9 |
| Compound A + 3a | 75 + 25 | 0.2 |
|  | 100 + 25 | 1.5 |
|  | 100 + 25 | 2.8 |
| Non-treated zone | — | 100 |

Biological Test Example 6

Test for *Myzus persicae*

Leaves on which the first instar of *Myzus persicae* were parasitic, were immersed in the test solutions of given concentrations which were prepared in accordance with the above-mentioned Formulation Example 2 (Emulsion), for 10 seconds. After air-drying, thus treated leaves were kept at 25° C. in a polyethylene cup. 6 Days after the drug treatment, surviving numbers of *Myzus persicae* were confirmed to determine the survival rate, which was calculated from the following equation.

$$\text{Survival rate } (\%) = (C_0 \times T_6 / T_0 \times C_6) \times 100 \quad \text{Equation 5}$$

wherein $C_0$ and $C_6$ respectively stand for number for larvae in the non-treated zone before the drug treatment and after 6 days, and $T_0$ and $T_6$ respectively stand for numbers of larvae in the treated zone before treatment and 6 days after the treatment.

Results thus obtained are shown in Table 6.

TABLE 6

| Test Compound | Amount of active component (ppm) | Survival rate (%) |
| --- | --- | --- |
| Compound A + 1 | 1 + 10 | 2.0 |
| Compound A + 2a | 1 + 10 | 3.0 |
| Compound A + 3a | 1 + 10 | 0.0 |
| Compound A + 4a | 1 + 10 | 1.0 |
| Compound A + 5a | 1 + 10 | 1.0 |
| Compound A | 1 | 34.1 |
| Compound 1 | 10 | 71.2 |
| Compound 2a | 10 | 70.5 |
| Compound 3a | 10 | 63.4 |
| Compound 4a | 10 | 65.5 |
| Compound 5a | 10 | 68.6 |
| Non-treated zone | — | 100 |

Biological Test Example 7

Test for *Tetranychus urticae*

15 female adults of *Tetranychus urticae* were allowed to lay eggs on a leaf disc of *Phaseolus vulgaris* of 2 cmφ. Next day given quantities of the drug solutions of given concentrations which were prepared according to the Formulation Example 2 (Emulsion) were sprayed to the leaf disc bearing both eggs and female adults. Immediately after the spraying, thus treated leaf disc was placed on a non-treated leaf disc of 5 cmφ. 2 Days after the treatment all the adults were removed from the leaves. Then 5 days after the treatment numbers of eggs and larvae on the non-treated leaf were counted to determine the survival rate of the second generation.

The survival rate was calculated from the following equation.

$$\text{Survival rate } (\%) = T/C \times 100$$

wherein C stands for the total number of the individuals in the non-treated zone after 5 days from the treatment and T stands for the total number of the individuals in the treated zone 5 days after the treatment.

Results thus obtained are shown in Table 7. Meanwhile compounds used as controls in the test are represented by the same compound symbols as above.

TABLE 7

| Test Compound | Amount of active component (ppm) | Survival rate (%) |
| --- | --- | --- |
| Compound A + X | 25 + 100 | 24.7 |
| Compound A + Y | 25 + 100 | 27.1 |
| Compound A + 3a | 25 + 100 | 1.5 |
| Compound A + 4a | 25 + 100 | 8.3 |
| Compound A + 5a | 25 + 25 | 1.6 |
|  | 25 + 100 | 0.3 |
| Non-treated zone | — | 100 |

Biological Test Example 8

Pot-Plant Test for *Tetranychus kanzawai*

A piece of leaf on which *Tetranychus kanzawai* were parasitic was inoculated to *Phaseolus vulgaris* in a primary leaf stage, and planted in a pot. 3 Days after the inoculation, the leaf piece was removed from *Phaseolus vulgaris*, to which a given quantity of the test solutions of given concentrations prepared according to the Formulation Example 2 (Emulsion) were sprayed (two replicates). During the test period the pot was kept at room temperature and the numbers of the female adults were counted on predetermined days to determine the prevention rate.

The prevention rate and the theoretical prevention rate were calculated from the following equation.

Prevention rate (%)=[1−{($T_4+T_9$)×$C_0$/($C_4+C_9$)× $T_0$}]×100 wherein $C_0$, $C_4$ and $C_9$ respectively stand for number of female adults in the non-treated zone before treatment, 4 days and 9 days after the treatment, and $T_0$, $T_4$ and $T_9$ respectively stand for number of female adults in the treated zone before treatment, 4 days and 9 days after the treatment.

Theoretical prevention rate (%)=$A$+{(100−$A$)× $B$}/100 wherein A stands for the prevention rate (%) of Compound A and B stands for the each prevention rate (%) of Compounds 3a–5a and Compounds X and Y.

Thus obtained results are shown in Table 8. Meanwhile compounds used in the test as controls are represented by the same compound symbols as used before.

TABLE 8

| Test Compound | Amounts of active components (ppm) | Prevention rate (%) | Theoretical prevention rate (%) |
|---|---|---|---|
| Compound A + 3a | 25 + 25 | 99.2 | 86.0 |
| Compound A + 4a | 25 + 25 | 99.1 | 90.7 |
| Compound A + 5a | 25 + 25 | 100 | 100 |
| Compound A + X | 25 + 25 | 81.8 | 89.9 |
| Compound A + Y | 25 + 25 | 62.2 | 61.2 |
| Compound A | 25 | 39.3 | — |
| Compound 3a | 25 | 77.0 | — |
| Compound 4a | 25 | 84.6 | — |
| Compound 5a | 25 | 100 | — |
| Compound X | 25 | 83.4 | — |
| Compound Y | 25 | 36.1 | — |

Biological Test Example 9

Pot-Plant Test for *Tetranychus kanzawai*

The test was conducted in the same manner as in Test Example 8 using *Tetranychus kanzawai*. The prevention rate and theoretical prevention rate were determined from the following equation.

Prevention rate (%)=[1−{($T_4+T_8+T_{14}+T_{18}+T_{22}$)×$C_0$ /($C_4+C_8+C_{14}+C_{18}+C_{22}$)×$T_0$}]×100 wherein $C_0$, $C_4$, $C_8$, $C_{14}$, $C_{18}$ and $C_{22}$ respectively denote numbers of female adults in the non-treated zone before treatment, and 4 days, 8 days, 14 days, 18 days and 22 days after the treatment, and $T_0$, $T_4$, $T_8$, $T_{14}$, $T_{18}$ and $T_{22}$ respectively denote numbers of female adults in the treated zone before treatment, and 4 days, 8 days, 14 days, 18 days and 22 days after the treatment.

Theoretical prevention rate (%)= $A$+{(100−$A$)×$B$}/100 wherein A denotes the prevention rate (%) of Compound A and B denotes the prevention rate (%) of Compounds 3a– 5a and Compounds X and Y respectively.

Thus obtained results are shown in Table 9. Meanwhile compounds used as controls in the test, are represented by the same compound symbols as used before.

TABLE 9

| Test Compound | Amounts of active components (ppm) | Prevention rate (%) | Theoretical prevention rate (%) |
|---|---|---|---|
| Compound A + 3a | 3.13/3.13 | 96.9 | 89.1 |
| | 12.5/12.5 | 99.3 | 92.1 |
| Compound A | 3.13 | 84.3 | — |
| | 12.5 | 84.9 | — |
| Compound 3a | 3.1 | 30.4 | — |
| | 12.5 | 47.6 | — |

What is claimed is:

1. An insecticidal and miticidal composition comprising, synergistic effective amounts of 2-(2,6-difluorophenyl)-4-(2-ethoxy-4-tertiarybutylphenyl)-2-oxazoline and at least one pyrethroid compound selected from the following compound group consisting of
(1) cyano(3-phenoxyphenyl)methyl 2,2-dimethyl-3-[ 3-oxo-3-{2,2,2-trifluoro-1-(trifluoromethyl)ethoxy}-1-propenyl] cyclopropanecarboxylate,
(2) α-cyano-3-phenoxybenzyl 2,2,3,3-tetramethylcyclopropanecarboxylate,
(3) α-cyano-3-phenoxybenzyl N-( 2-chloro-α,α,α-trifluoro-p-tolyl) valinate, and
(4) 2-methylbiphenyl-3-ylmethyl 3-(2-chloro-3,3,3-trifluoroprop- 1-enyl)-2,2-dimethylcyclopropanecarboxylate wherein 0.01–30 parts by weight of the pyrethroid compound is mixed with 1 part of the oxazoline compound.

2. The insecticidal and miticidal composition according to claim 1, wherein the pyrethroid compound is cyano (3-phenoxyphenyl)methyl 2,2-dimethyl-3-(3-oxo-3-{2,2,2-trifluoro-1-(trifluoromethyl)ethoxy} -1-propenyl)cyclopropanecarboxylate.

3. The insecticidal and miticidal composition according to claim 1, wherein the pyrethroid compound is α-cyano-3-phenoxybenzyl 2,2,3,3-tetramethylcyclopropanecarboxylate.

4. The insecticidal and miticidal composition according to claim 1, wherein the pyrethroid compound is α-cyano-3-phenoxybenzyl N-(2-chloro-α,α,α-trifluoro-p-tolyl)valinate.

5. The insecticidal and miticidal composition according to claim 1, wherein the pyrethroid compound is 2-methylbiphenyl-3-ylmethyl 3-(2-chloro-3,3,3-trifluoroprop-1-enyl)-2,2-dimethylcyclopropanecarboxylate.

6. The composition according to claim 1, wherein said pyrethroid compound is present in an amount of 0.1–20 parts by weight.

7. The composition according to claim 1, wherein said pyrethroid compound is present in an amount of 1–4 parts by weight.

8. A method for controlling insects and mites, which comprises applying the synergistic insecticidally or miticidally effective amount of the composition according to claim 1 to the locus where noxious insects or mites propagate.

9. The method for controlling insects and mites according to claim 3, wherein the composition is applied in an amount of 0.1–1000 g per 10a in terms of the total active ingredients.

10. The method according to claim 8, wherein said pyrethroid compound is present in an amount of 0.1–20 parts by weight.

11. The method according to claim 8, wherein said pyrethroid compound is present in an amount of 1–4 parts by weight.

* * * * *